United States Patent [19]
Valente et al.

[11] Patent Number: 5,932,778
[45] Date of Patent: Aug. 3, 1999

[54] SHUTDOWN PROCESS FOR OLEFIN POLYMERIZATION REACTOR

[75] Inventors: Anthony M. Valente, Yorktown; David B. Johnson, Hayes, both of Va.; George A. Huff, Jr., Naperville, Ill.

[73] Assignee: BP Amoco Corporation, Chicago, Ill.

[21] Appl. No.: 08/940,509

[22] Filed: Sep. 30, 1997

[51] Int. Cl.⁶ ..................................... C07C 2/02
[52] U.S. Cl. .................. 585/529; 585/502; 585/520; 585/527; 585/950
[58] Field of Search ..................... 585/502, 520, 585/527, 529, 950

[56] References Cited

U.S. PATENT DOCUMENTS

| | | | |
|---|---|---|---|
| 2,120,702 | 6/1938 | Ipatieff et al. | 23/233 |
| 2,658,933 | 11/1953 | May et al. | 250/683.15 |
| 3,050,472 | 8/1962 | Morrell | 252/435 |
| 3,050,473 | 8/1962 | Morrell | 252/435 |
| 3,132,109 | 5/1964 | Morrell | 252/435 |
| 4,028,430 | 6/1977 | Stine et al. | 260/683.43 |
| 4,062,801 | 12/1977 | Burton et al. | 252/414 |
| 4,857,666 | 8/1989 | Barger et al. | 585/323 |
| 5,648,579 | 7/1997 | Kulprathipanja et al. | 585/447 |

FOREIGN PATENT DOCUMENTS

| | | | |
|---|---|---|---|
| 1055921 | 6/1979 | Canada | B01J 27/14 |
| 863539 | 3/1961 | United Kingdom . | |

*Primary Examiner*—Glenn Caklarola
*Assistant Examiner*—In Suk Bullock
*Attorney, Agent, or Firm*—Richard A. Kretchmer; Frank J. Sroka

[57] ABSTRACT

A method is provided which can be used to quickly and easily take a fixed-bed of solid acid olefin polymerization catalyst out of service without causing any significant catalyst deactivation. The method involves substituting a substantially olefin-free hydrocarbon fluid for at least a portion of the olefin-containing feedstock to the polymerization process, wherein the substantially olefin-free hydrocarbon fluid boils within the range from about 20° to about 250° C. and contains at least about 5 vol. % aromatics.

22 Claims, No Drawings

SHUTDOWN PROCESS FOR OLEFIN POLYMERIZATION REACTOR

FIELD OF THE INVENTION

This invention relates to a process for polymerizing olefins over a fixed-bed of solid acid catalyst. More specifically, the invention is an improved method for taking such a fixed-bed of catalyst out of service from such a process without causing significant catalyst deactivation.

BACKGROUND OF THE INVENTION

A variety of commercial chemical and petrochemical processes involve the condensation reaction of an olefin or a mixture of olefins over an acid catalyst to form higher molecular weight products. This process is referred to herein as a polymerization process, and the products can be either low molecular weight oligomers or high molecular weight polymers. Oligomers are formed by the condensation of 2, 3 or 4 olefin molecules with each other, while polymers are formed by the condensation of 5 or more olefin molecules with each other. As used herein, the term "polymerization" is used to refer to a process for the formation of oligomers and/or polymers.

Low molecular weight olefins (such as propene, 2-methylpropene, 1-butene and 2-butene) can be converted by polymerization over a solid acid catalyst (such as a solid phosphoric acid catalyst) to a product which is comprised of oligomers and is of value as a high-octane gasoline blending stock and as a starting material for the production of chemical intermediates and end-products which include alcohols, detergents and plastics. Such a process is typically carried out over a fixed-bed of solid acid catalyst and at elevated temperatures and pressures in either a chamber reactor or a tubular reactor. A plurality of reactors is ordinarily used in the practice of such a process so that individual reactors can be taken out of service for catalyst replacement or other maintenance without shutting down the other reactors of the process unit. In addition, reaction conditions in the process unit may be optimized through the use of two or more reactors in series.

The acid catalyzed alkylation of aromatic compounds with olefins is a well-known reaction which is of commercial importance. For example, ethylbenzene, cumene and detergent alkylate are produced by the alkylation of benzene with ethylene, propylene and $C_{10}$ to $C_{18}$ olefins, respectively. Sulfuric acid, HF, phosphoric acid, aluminum chloride, and boron fluoride are conventional catalysts which are useful for this reaction. In addition, solid acids which have a comparable acid strength can also be utilized to catalyze this process, and such materials include amorphous and crystalline aluminosilicates, clays, ion-exchange resins, mixed oxides and supported acids such as solid phosphoric acid catalysts.

When a fixed-bed of solid acid catalyst is used to catalyze the polymerization of olefins, great care must be taken to avoid deactivation of the catalyst. For example, small amounts of basic impurities in the feedstock can undergo chemical reaction with the acid catalyst and cause its deactivation. In addition, the reaction conditions must be carefully controlled to prevent the deposition of extremely high molecular weight products on the catalyst surface which will deactivate the catalyst. An undesirable increase in the pressure drop across the catalyst bed can also occur simultaneously with catalyst deactivation. It is particularly difficult to rapidly take a polymerization reactor out of service without causing undesirable catalyst deactivation.

In the operation of a petroleum refinery, a major source of olefins for an olefin polymerization unit will typically be a fluidized catalytic cracking unit. Any upset of the catalytic cracking unit or any other process unit that provides these olefins will, ordinarily, result in a reduced supply of olefins for the polymerization unit and will require that one or more of the process unit reactors be taken out of service. In the case of a polymerization unit that is operated using a solid phosphoric acid catalyst in a plurality of fixed-bed reactors, it is very difficult to rapidly take the reactors out of service without causing significant catalyst deactivation. A conventional shutdown procedure for such a unit, when attempting to save catalyst activity in the reactors, has been to recycle propane in the unit and then take the individual reactors off-line. Each individual reactor is then depressurized, residual hydrocarbons removed under vacuum, and the reactor purged with an inert gas such as nitrogen. Finally, the reactors are "blinded" by inserting a metal plate at the site of each valve which controls the flow of hydrocarbons through the reactors. This metal plate acts as a plug to prevent any possible leakage of hydrocarbons through the valve. Although catalyst activity can survive this type of shutdown procedure, catalyst coking is frequently observed as a consequence of the shutdown. It is not uncommon for catalyst deactivation to take place in at least one reactor of a polymerization unit which contains about eight tubular reactors and, occasionally, catalyst deactivation can take place in all of the reactors when the unit is shut down in this manner. For a conventional polymerization unit, this type of shutdown procedure can take as long as 16 hours.

Canadian Patent No. 1,055,921 (Burton et al.) discloses that a bed of solid phosphoric acid catalyst which has been deactivated by the deposition on the catalyst particles of polymerized and carbonized hydrocarbonaceous materials can be reactivated in situ by: (a) inundating the deactivated catalyst at a temperature of 40 to 370° C. and pressure of $1\frac{1}{3}$ to 100 atmospheres, absolute, in a reactivating liquid of a mixture of hydrocarbons which is substantially free from sulfur, which contains at least 5 weight percent aromatics and which boils within the range of 40 to 230° C.; (b) withdrawing the reactivating liquid from the catalyst; and (c) repeating steps (a) and (b), above, at least one time. It is further disclosed that the deactivated catalyst can be from a polymerization unit for production of motor fuel from light olefinic gases and that catalytic reformate can be used as the reactivating liquid.

Summary of the Invention

In the operation of a petroleum refinery, a major source of the olefins for a polymerization unit will typically be a fluidized catalytic cracking unit. Any upset of the catalytic cracking unit or any other process unit that provides this feedstock will ordinarily result in a reduced supply of olefins for the polymerization unit and may require that one or more of the polymerization unit reactors be taken out of service. Accordingly, it is important that a method be available for quickly taking such reactors out of service without causing any significant catalyst deactivation. Using prior art procedures, it has been very difficult to temporarily take a polymerization reactor out of service when the reactor contains a fixed-bed of solid acid catalyst. We have discovered a method which can be used to take such a fixed-bed solid acid catalyst out of service within the space of a few minutes and without any significant catalyst deactivation. The method of this invention is particularly satisfactory for use in the shutdown of a fixed-bed of solid phosphoric acid catalyst in an olefin polymerization reactor.

One embodiment of the invention is a process for taking a fixed-bed of solid acid catalyst out of use without causing any significant catalyst deactivation, wherein said catalyst bed is used to catalyze the polymerization of olefins in an olefin-containing feedstock, and wherein said method comprises: (a) substituting a modified feedstock for the olefin-containing feedstock, wherein said modified feedstock is prepared by substituting a substantially olefin-free hydrocarbon fluid for at least a portion of said olefin-containing feedstock, and wherein the substantially olefin-free hydrocarbon fluid boils within the range from about 20°0 to about 250° C. and contains at least about 5 vol. % aromatics; and (b) terminating the flow of said modified feedstock to the fixed-bed of catalyst after the contents of the fixed-bed have been displaced by the modified feedstock and any products derived from it, and wherein the amount of said substantially olefin-free hydrocarbon fluid used to prepare the modified feedstock is effective to prevent any significant deactivation of the fixed-bed of catalyst during said process.

An object of the invention is to provide a method for taking a fixed-bed of solid acid catalyst out of service as an olefin polymerization catalyst without causing significant deactivation of the catalyst.

An object of the invention is to provide a method for taking a fixed-bed of solid phosphoric acid catalyst out of service as an olefin polymerization catalyst without causing significant deactivation of the catalyst.

An object of the invention is to provide a rapid method for taking a fixed-bed of solid acid catalyst out of service as an olefin polymerization catalyst.

A further object of the invention is to reduce the amount of labor required for taking a fixed-bed of solid acid polymerization catalyst out of service.

Detailed Description of the Invention

The present invention relates to a process for polymerizing olefins over a fixed-bed of solid acid catalyst and is directed to a method which can be used to quickly and easily take such a fixed-bed of catalyst out of service without causing significant deactivation of the catalyst. The method involves replacing at least a portion of the of olefin-containing feedstock to the catalyst bed with a substantially olefin-free hydrocarbon liquid which contains at least about 5 vol. % aromatics. This simple substitution of an aromatic containing hydrocarbon liquid for some or all of the olefin-containing feedstock permits an almost instantaneous shutdown of the catalyst bed without any attendant risk of catalyst deactivation.

The olefin-conversion process of this invention can be carried out with cyclic olefins, substituted cyclic olefins, and olefins of formula I wherein $R_1$ is a hydrocarbyl group and each $R_2$ is independently selected from the group consisting of hydrogen and hydrocarbyl groups. Preferably, $R_1$ is an alkyl group and each $R_2$ is independently selected from the group consisting of hydrogen and alkyl groups. Examples of suitable cyclic olefins and substituted cyclic olefins include cyclopentene, 1-methylcyclopentene and cyclohexene. Examples of suitable olefins of the type of formula I include propene, 2-methylpropene, 1-butene, 2-butene, 2-methyl-1-butene, 3-methyl-1-butene, 2-methyl-2-butene, 2,3-dimethyl-1-butene, 3,3-dimethyl-1-butene, 2,3-dimethyl-2-butene, 2-ethyl-1-butene, 1-pentene, 2-pentene, 2-methyl-1-pentene, 3-methyl-1-pentene, 4-methyl-1-pentene, 1-hexene, 2-hexene, and 3-hexene.

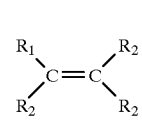

Preferred olefins for use in the practice of the olefin-conversion process of this invention will contain from 3 to 6 carbon atoms, and highly preferred olefins will contain 3 or 4 carbon atoms. If desired, the olefin-containing feedstock for the olefin-conversion process can comprise a mixture of different olefins. Alternatively, the feedstock can be comprised of a single olefin. It will be appreciated that the olefin-containing feedstock can comprise materials other than olefins, such as diluents which are substantially inert under the reaction conditions utilized in the polymerization process. For example, the feedstock can contain substantial quantities of saturated hydrocarbons, such as normal paraffins, which will be relatively unreactive under the conditions of the olefin-conversion process. Indeed, a normal paraffin such as propane or butane can be used as a diluent and as a recycle material for use in managing the heat which is produced by the exothermic polymerization reaction. A typical olefin-containing feedstock to a polymerization unit for conversion to oligomers in the gasoline boiling range will typically comprise a mixture of propane, butane, 1-methylpropane, propene, 1-butene, 2-butene and 1-methylpropene, wherein the olefin concentration is in the range from about 35 vol. % to about 60 vol. %. However, it will be appreciated that olefin concentrations can be used which are outside of this range.

In a preferred embodiment of the invention, the olefin-containing feedstock which is used in the practice of this invention will be substantially free of aromatic hydrocarbons. However, if desired, the olefin-containing feedstock can comprise one or more aromatic compounds. When aromatic components are present, alkylation of these components by the olefin or olefins of the feedstock can be carried out simultaneously with olefin polymerization. However, the olefin-containing feedstock should not contain a concentration of aromatic compounds which is so high that the formation of products from alkylation of the aromatic compounds predominates over the formation of olefin polymerization products. Desirably, the mole ratio of olefins to aromatic compounds in the olefin-containing feedstock will be at least about 12, preferably at least about 15, and more preferably at least about 18. In such an embodiment, volatile low molecular weight aromatic compounds such as benzene, which are undesirable as gasoline components because of toxicity considerations, can be converted to less volatile materials, which are highly desirable gasoline components, by alkylation in a polymerization unit. For example, benzene and toluene can be converted to cumene and cymene, respectively, by monoalkylation with propene. Such a blending of polymerization and alkylation is a particularly desirable process for use in the manufacture of gasoline blending stock. In such an embodiment, low molecular weight olefins which contain from 3 to 4 carbon atoms can be used to alkylate benzene, and excess olefins are converted to oligomers. All of these products are of high octane and are desirable gasoline components.

Aromatic compounds which can be included in the olefin-containing feedstock to the polymerization unit include all organic compounds of from 6 to 20 carbon atoms which contain aromatic functionality and can be alkylated by an olefin in the presence of an acid catalyst. Such materials include both aromatic compounds and substituted aromatic compounds which carry one or more substituents. Aromatic hydrocarbons and hydrocarbyl-substituted aromatic hydrocarbons which contain from 6 to 10 carbon atoms are particularly suitable. In addition, mixtures of such materials can be used as a component of the feedstock in the practice of this invention. Examples of such materials include compounds of formula II which contain from 6 to 20 carbon atoms where each R is independently selected from the group consisting of hydrogen and hydrocarbyl groups. However, preferred aromatic compounds are hydrocarbons which contain from 6 to 10 carbon atoms and are of formula II where each R is independently selected from the group consisting of

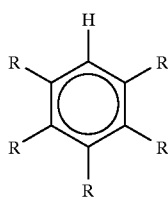

(II)

hydrogen and alkyl of from 1 to 3 carbon atoms. Benzene and toluene are particularly preferred aromatic substrates for conversion to gasoline blending stock by alkylation with low molecular weight olefins.

Aromatic compounds for inclusion in the olefin-containing feedstock to the olefin polymerization process can be obtained from any desired source. However, when gasoline blending stocks are manufactured in a petroleum refinery through the use of the olefin polymerization process, catalytic cracking units, reformers and isomerization units are convenient sources of the aromatic components. For example, a light reformate can be used, and a typical material of this type will have a total aromatic content of about 35 vol. %, and it will contain about 10 vol. % of benzene. If an olefin-containing feedstock is prepared by combining about 10 vol. % of such a light reformate with about 90 vol. % of a $C_3$ to $C_4$ feedstock which contains about 45 vol. % of propylene and butylenes which are mixed with propane and butanes, about 80% of the benzene in this feedstock can be alkylated in a conventional olefin polymerization unit which uses a solid phosphoric acid catalyst.

Any solid acidic material which can catalyze the polymerization of an olefin can be used as a catalyst in the practice of this invention, and such materials include liquid acids which are supported on a solid substrate. In the practice of the olefin polymerization process, the olefin-containing feedstock can simply be passed through a particulate fixed-bed of a solid acidic catalyst at a suitable temperature and pressure.

Catalysts which are suitable for use in the practice of the invention can be comprised of materials such as acidic polymeric resins, supported acids, and acidic inorganic oxides. Suitable acidic polymeric resins include the polymeric sulfonic acid resins which are well-known in the art and are commercially available. Amberlyst® 35, a product produced by Rohm and Haas Co., is a typical example of such a material.

Supported acids which are useful as catalysts include, but are not limited to, Brönsted acids (examples include phosphoric acid, sulfuric acid, boric acid, HF, fluorosulfonic acid, trifluoromethanesulfonic acid, and dihydroxyfluoroboric acid) and Lewis acids (examples include $BF_3$, $BCl_3$, $AlCl_3$, $AlBr_3$, $FeCl_2$, $FeCl_3$, $ZnCl_2$, $SbF_5$, $SbCl_5$ and combinations of $AlCl_3$ and HCl) which are supported on solids such as silica, alumina, silica-aluminas, zirconium oxide or clays. When liquid acids are employed, the supported catalysts are typically prepared by combining the desired liquid acid with the desired support and drying.

Acidic inorganic oxides which are useful as catalysts include, but are not limited to, aluminas, silica-aluminas, natural and synthetic pillared clays, and natural and synthetic zeolites such as faujasites, mordenites, L, omega, X, Y, beta, and ZSM zeolites. Highly suitable zeolites include beta, Y, ZSM-3, ZSM-4, ZSM-5, ZSM-18, and ZSM-20. If desired, the zeolites can be incorporated into an inorganic oxide matrix material such as a silica-alumina.

Catalysts can comprise mixtures of different materials, such as a Lewis acid (examples include $BF_3$, $BCl_3$, and $AlCl_3$), a nonzeolitic solid inorganic oxide (such as silica, alumina and silica-alumina), and a large-pore crystalline molecular sieve (examples include zeolites, pillared clays and aluminophosphates).

Supported catalysts which are prepared by combining a phosphoric acid with a support are often used in olefin polymerization processes and are highly preferred for use in the practice of this invention. Such catalysts are referred to herein as solid phosphoric acid catalysts.

A solid phosphoric acid catalyst is normally prepared by mixing a phosphoric acid, such as ortho-phosphoric acid, pyro-phosphoric acid or tetra-phosphoric acid, with a siliceous solid carrier to form a wet paste. This paste may be calcined and then crushed to yield catalyst particles, or the paste may be extruded or pelleted prior to calcining to produce more uniform catalyst particles. The carrier is typically a naturally occurring porous silica-containing material such as kieselguhr, kaolin, infusorial earth or diatomaceous earth. A minor amount of various additives, such as mineral talc, fullers earth and iron compounds, including iron oxide, can be added to the carrier to increase its strength and hardness. The combination of the carrier and the additives normally comprises about 15–30 wt. % of the catalyst, with the remainder being the phosphoric acid. However, the amount of phosphoric acid used in the manufacture of the catalyst can vary from about 8–80 wt. % of the catalyst. Solid phosphoric catalysts are available commercially, and such a material is available from UOP under the name SPA-2 which is a cylindrical extrudate having the following properties: (1) a nominal diameter of 4.75 mm; (2) a loaded density of 0.93 g/cm$^3$; (3) a free phosphoric acid content, calculated as $P_2O_5$, of 16 to 20 wt. %; and (4) a nominal total phosphoric acid content, calculated as $P_2O_5$, of 60 wt. %. The preparation and properties of conventional solid phosphoric acid catalysts are set forth in U.S. Pat. No. 2,120,702 (Ipatieff et al.), U.S. Pat. No. 3,050,472 (Morrell); U.S. Pat. No. 3,050,473 (Morrell) and U.S. Pat. No. 3,132,109 (Morrell); and also in British Patent No. 863,539. These patents are incorporated herein by reference.

In the practice of the olefin polymerization process of this invention, an olefin-containing feedstock is contacted with the solid acid catalyst at a temperature and pressure for a period of time which are effective to result in conversion of at least a portion of the olefins in the feedstock to the desired products, such as oligomers which are useful as a gasoline blending stock or as a petrochemical feedstock. Desirably, the contacting temperature will be in excess of about 50° C., preferably in excess of 100° C., and more preferably in excess of 125° C. The contacting will generally be carried out at a temperature in the range from about 50° to about 350° C., preferably from about 100° to about 350° C., and more preferably from about 125° to about 250° C. It will be appreciated, of course, that the optimum temperature will be a function of the specific solid acid catalyst used and the specific olefins and their concentration in the feedstock. However, for typical solid phosphoric acid catalysts used in combination with propylene and/or butylenes, the reaction temperature will usually be in the range from about 150° to about 250° C.

In the practice of the olefin polymerization process of this invention, the olefin-containing feedstock can be contacted with the solid acid catalyst at any suitable pressure. However, pressures in the range from about 0.01 to about 200 atmospheres are desirable, and a pressure in the range from about 1 to about 100 atmospheres is preferred. When a typical solid phosphoric acid catalyst is used for the conversion of propylenes and/or butylenes to gasoline blending stock by polymerization, the pressure will usually be in the range from about 20 to about 90 atmospheres.

The olefin polymerization process of this invention can be carried out over a fixed-bed of the solid acid catalyst which can be located in either a chamber reactor or tubular reactor. In a tubular reactor, the catalyst is contained in a multiplicity of small tubes which are surrounded with a circulating cooling medium. These tubes will typically have an internal diameter of from about 5 cm to about 15 cm, although other diameters can also be used. A tubular reactor is frequently preferable to a chamber reactor because it permits a closer control of the reaction temperature and can be easily constructed for high pressure operation. Ordinarily, a plurality of reactors will be used. For example, an olefin polymerization unit employing tubular reactors can have as many as eight or more reactors. The heat produced by the exothermic polymerization reaction can be controlled in a chamber reactor by using a saturated hydrocarbon as a recycle from reactor effluent to reactor feedstock and/or as a quench between multiple catalyst beds within a chamber reactor. The temperature in tubular reactors is typically controlled by water or oil circulation around the reactor tubes.

When a solid acid catalyst is used for the polymerization of olefins, the catalyst undergoes slow deactivation as a result of undesired products which accumulate on the surface of the catalyst and in catalyst pores. These undesired products have the effect of encapsulating the catalyst and thereby hinder or prevent fresh reactants in the feedstock from contacting the catalyst. However, when a fixed-bed of solid acid polymerization catalyst is temporarily taken out of service using conventional procedures, a rapid coking or other deactivation of the catalyst often takes place.

In the practice of this invention, a fixed-bed of solid acid catalyst is taken out of service by charging a modified feedstock to the fixed-bed, wherein the modified feedstock is prepared by replacing at least a portion of the olefin containing feedstock with a substantially olefin-free hydrocarbon fluid which boils within the range from about 40° to about 250° C. and contains at least about 5 vol. % aromatics. This substitution of the modified feedstock for the original olefin-containing feedstock is carried out under the ordinary conditions of temperature and pressure which are used for the olefin polymerization process. In one embodiment of the invention, a substantially constant flow of fluid is maintained through the fixed-bed of catalyst at olefin polymerization conditions while substituting the modified feedstock for the original olefin-containing feedstock.

Although the substantially olefin-free hydrocarbon fluid can boil within the broad range from about 20° to about 250° C., a preferred range is from about 20° to about 180° C., and a highly preferred range is from about 30° to about 130° C. In addition, this fluid will contain, desirably at least about 5 vol. % of aromatics, preferably at least about 20 vol. % of aromatics, and more preferably at least about 30 vol. % of aromatics. Typically, this fluid will contain from about 15 to about 85 vol. % aromatics. Finally, the substantially olefin-free hydrocarbon fluid will have an olefin content which is desirably less than 5 vol. %, preferably less than 3 vol. %, and more preferably less than 2 vol. %.

In a petroleum refinery, the substantially olefin-free hydrocarbon fluid can be selected from the group consisting of naphthas, reformates and blends of aromatic and aliphatic hydrocarbons and, preferably, it will be a reformate. A typical light reformate which is highly suitable for use in the practice of this invention will contain from about 0 to about 2 vol. % olefins, from about 20 to about 45 vol. % aromatics, and will have distillation properties such that the 10% distillation point ("T10") is no greater than about 160° F. (71° C.), the 50% distillation point ("T50") is no greater than about 200° F. (93° C.), and the 90% distillation point ("T90") is no greater than about 250° F. (121° C.). It will be understood that these distillation points refer to a distillation point obtained by the ASTM D 86-95 procedure (which can be found in the 1996 Annual Book of ASTM Standards, Section 5, Petroleum Products, Lubricants, and Fossil Fuels) or by conventional alternative procedures. A typical light reformate will typically contain from about 5 to about 15 vol. % of benzene.

The aromatics of the substantially olefin-free hydrocarbon fluid are of critical importance in the practice of this invention. Aromatic compounds which are suitable as components of this fluid include all organic compounds of from 6 to 10 carbon atoms which contain aromatic functionality and can be alkylated by an olefin in the presence of an acid catalyst. Such materials include both aromatic compounds and substituted aromatic compounds which carry one or more substituents. Aromatic hydrocarbons and hydrocarbyl-substituted aromatic hydrocarbons which contain from 6 to 10 carbon atoms are particularly suitable. In addition, mixtures of such materials can be used as components of the substantially olefin-free hydrocarbon fluid in the practice of this invention. Examples of such materials include compounds of formula II which contain from 6 to 20 carbon atoms where each R is independently selected from the group consisting of hydrogen and hydrocarbyl groups. However, preferred aromatic compounds are hydrocarbons which contain

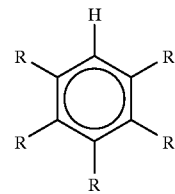

(II)

from 6 to 10 carbon atoms and are of formula II where each R is independently selected from the group consisting of hydrogen and alkyl of from 1 to 3 carbon atoms. Benzene and toluene are particularly preferred as aromatic components of the substantially olefin-free hydrocarbon fluid.

The modified feedstock of this invention is prepared by substituting the substantially olefin-free hydrocarbon fluid for at least a portion of the olefin-containing feedstock wherein the amount of said fluid is effective to prevent any significant deactivation of the fixed-bed catalyst when the flow of hydrocarbons through it is terminated. Desirably, the modified feedstock of this invention will contain at least about 20 vol. % of the substantially olefin-free hydrocarbon fluid, and preferably the amount will be at least about 40 vol. %. Although the modified feedstock can contain as much as 100 vol. % of the substantially olefin-free hydrocarbon fluid, the amount will typically be in the range from about 20 to about 90 vol. % and more typically in the range from about 20 to about 70 vol. %. The mole ratio of olefins to aromatics in the resulting modified feedstock should be less than about 10, preferably less than about 7, and more preferably less than about 5.

Since the temperature in the fixed-bed of catalyst is usually maintained by the heat generated by the exothermic polymerization reaction, the substitution of the substantially olefin-free hydrocarbon fluid for a portion of the olefin-containing feedstock will result in some reduction of the fixed-bed temperature because of a reduced amount of olefin polymerization, which is a consequence of the reduced olefin concentration. Once the contents of the fixed-bed of catalyst have been displaced by the modified feedstock and any products derived from it as a consequence of contact with the catalyst of the fixed-bed, the temperature of the fixed-bed can be further reduced to any desired value. For example, the temperature can be reduced to ambient or to a value which is below that which is required to sustain rapid polymerization of the olefins in the olefin-containing feedstock. In addition, the pressure within the fixed-bed of catalyst can be reduced to any desired value as soon as the displacement of the fixed-bed contents has been completed. If desired, both the temperature and pressure within the fixed-bed of catalyst can be reduced to any desired level as soon as said displacement of the fixed-bed contents has been completed. In addition, the fluid hydrocarbon contents of the fixed-bed can be removed, if desired, as soon as the displacement is completed. For example, the fixed-bed can be evacuated and then purged with an inert gas such as nitrogen.

The olefin-containing feedstock and products derived from it are displaced from the fixed-bed of solid acid catalyst that is to be taken out of service by the modified feedstock and any products that are formed upon contact of the modified feedstock with the fixed-bed of catalyst. The fixed-bed of solid acid catalyst is no longer susceptible to deactivation when this displacement is completed. Accordingly, the flow of modified feedstock to the fixed-bed of catalyst can be terminated as soon as the displacement is complete.

Although the mechanism by which catalyst deactivation takes place during conventional reactor shutdown procedures is unknown, it is believed that olefins undergo conversion to undesired high boiling polymers under the non-optimal conditions that prevail during shutdown. These high boiling polymers can then remain on the catalyst and undergo further conversion to even higher molecular weight polymers which resemble heavy tars and, in some cases, even have the appearance of a coke-like material. These materials can coat the catalyst particles and plug pores in the catalyst, thereby causing catalyst deactivation. During conventional shutdown procedures, attempts are made to rapidly minimize the concentration of olefins in the reactor while the temperature is reduced. However, in practice, this is quite difficult. For example, a conventional shutdown procedure involves the recycle of propane in the reactor. However, this propane is usually contaminated with significant amounts of propylene, and it is believed that this propylene results in the frequently observed catalyst deactivation by undergoing polymerization to heavy polymers and/or tars. Although the mechanism by which this invention operates is unknown, it is believed that three principal factors are involved. First of all, a substitution of the substantially olefin-free hydrocarbon fluid of this invention for at least a portion of the olefin-containing feedstock serves to reduce the concentration of olefins in the reactor and, accordingly, reduce the risk of undesired conversion of the remaining olefins to high boiling polymer and tars. Second, the substantially olefin-free hydrocarbon fluid is a better solvent than the original olefin-containing feedstock for the undesired polymers and tars that can cause catalyst deactivation. Accordingly, the substitution of this material for a portion of the original olefin-containing feedstock serves to keep these deactivating materials in solution and thereby prevents their deposition on the catalyst. Third, it is believed that the aromatic components of the substantially olefin-free hydrocarbon fluid of this invention help prevent the conversion of olefins to heavy polymers and tars since they serve as a substrate for residual olefins in the reactor to react with. That is to say, it is believed that the residual olefins in the reactor are partially consumed by alkylation of these aromatic hydrocarbons, thereby preventing the conversion of these olefins by polymerization to undesired heavy polymers and tars. Otherwise stated, it is believed that aromatic alkylation competes successfully with olefin polymerization for the residual olefins in the reactor and thereby prevents catalyst deactivation. In view of this competition of aromatic hydrocarbons for available olefins, it is not necessary to replace all of olefin-containing feedstock with the substantially olefin-free hydrocarbon fluid to shutdown a reactor in accordance with the practice of this invention.

Displacement of the olefin-containing feedstock and products derived from it with a modified feedstock in accordance with the practice of this invention can be carried out within the space of a few minutes. Therefore, this brief period of time is all that is required to take the fixed-bed of solid acid catalyst out service without causing any significant deactivation of it. In one embodiment of the invention, a substantially constant flow of fluid is maintained through the fixed-bed of solid acid catalyst at olefin conversion conditions while substituting the substantially olefin-free hydrocarbon fluid for at least a portion of the olefin-containing feedstock.

When the fixed-bed of solid acid catalyst is comprised of a solid phosphoric acid catalyst, a highly preferred embodiment of the invention is to use a substantially olefin-free hydrocarbon fluid which is substantially anhydrous in the practice of this invention. The activity of solid phosphoric acid catalysts is very sensitive to the degree of hydrolysis of the catalyst components.

After a temporary shutdown of a fixed-bed of solid acid catalyst in accordance with this invention, the fixed-bed can be put back into service for catalyzing the polymerization of olefins by the steps of: (a) adjusting the temperature and pressure of the fixed-bed of catalyst to a level suitable for olefin polymerization while said fixed-bed is filled with the modified feedstock; (b) displacing the modified feedstock with the olefin-containing feedstock at a flow rate suitable for olefin conversion; and (c) maintaining said flow of the olefin-containing feedstock under olefin polymerization conditions.

The following example is intended only to illustrate the invention and is not to be construed as imposing limitations on the invention.

EXAMPLE

The conversion of $C_3$ and $C_4$ olefins to high octane gasoline blending stock by conversion to dimers and trimers was carried out over a solid phosphoric acid catalyst (SPA-2 sold by UOP) in a polymerization unit which contained eight tubular reactors, one of which (Reactor D) was out of service at the time of this experiment. The feedstock to the unit was prepared by blending a minor amount of light reformate with an olefin-containing $C_3$–$C_4$ stream. The composition of the feedstock and operating conditions of the polymerization unit immediately prior to shutdown are set forth in Table I. The composition of the light reformate and of the olefin-containing $C_3$–$C_4$ streams are set forth in Table II.

One of the seven reactors (Reactor H) was taken out of service by conventional practice, which involved the recycle of propane in the reactor followed by depressurization, evacuation, and purging. The flow of light reformate to the remaining six reactors of the polymerization unit was then increased to a flow rate of about 1800 bpd (286,000 liters/day) while the flow of olefins to the reactors was reduced correspondingly. The flow of hydrocarbons to three of the reactors was then terminated, and these three reactors were immediately evacuated and purged.

The volume of light reformate charged to the unit was held constant while the flow of most of the olefin-containing $C_3$–$C_4$ stream to the reactors was terminated. Since only four reactors remained in service, this represented a substantially increased flow of light reformate to each of the remaining reactors. This flow was continued for about one hour. The flow of hydrocarbons to these four reactors was then terminated, and the reactors were evacuated and purged.

The activity of the catalyst in the reactors of the polymerization unit, both before shutdown and after shutdown, is set forth in Table III. Catalyst activity before shutdown was measured six days prior to unit shutdown, and catalyst activity after shutdown was measured one day after the unit was put back into service following the shutdown (the larger the number, the higher catalyst activity). The composition of the feedstock and operating conditions of the polymerization unit after being put back into service following the shutdown are set forth in Table I.

The data in Table III indicate that the shutdown procedure of this invention, which was used with reactors A, B, E and F, can be carried out without significant deactivation of the catalyst. More specifically, the catalyst in three of the reactors (reactors A, B and E) gained a small amount of activity, while the catalyst in one reactor (reactor F) lost a small amount of activity. Overall, the activity in these four reactors was substantially unchanged after the shutdown.

In contrast, the use of conventional shutdown procedures with this polymerization unit have usually resulted in the substantially complete deactivation of the catalyst in at least one of the eight reactors and, on occasion, in all eight reactors. It will be noted that some deactivation of the catalyst in reactor H was noted in this experiment wherein a conventional shutdown procedure was used.

TABLE I

Process Conditions in Olefin Polymerization Unit Prior to Shutdown and After Being Put Back in Service Following the Shutdown.

| Parameter or Variable | Before Shutdown | After Shutdown |
| --- | --- | --- |
| Reactors in Service | (Reactors A, B, C, B, F, G and H) | 7 (Reactors A, B, C, D, E, F and H) |
| Feedstock Flow Rates, bpd (liters/day) | | |
| Total Feedstock to Unit | 6,702 (1,065,500) | 6,508 (1,034,700) |
| Reactor A | 924 (146,900) | 860 (136,700) |
| Reactor B | 886 (140,900) | 785 (124,800) |
| Reactor E | 880 (139,900) | 1,084 (172,300) |
| Reactor F | 733 (116,500) | 635 (101,000) |
| Reactor H | 1,299 (206,500) | 1,013 (161,000) |

TABLE I-continued

Process Conditions in Olefin Polymerization Unit Prior to Shutdown and After Being Put Back in Service Following the Shutdown.

| Parameter or Variable | Before Shutdown | After Shutdown |
| --- | --- | --- |
| Feedstock Composition, vol. % | | |
| Olefin-containing $C_3$–$C_4$ Stream | 89.6 | 89.2 |
| Light Reformate Stream | 10.4 | 10.8 |
| Pressure, atmospheres gauge | | |
| Unit Inlet | 69.7 | 78.1 |
| Unit Outet | 64.3 | 69.9 |
| Inlet Temperature. °C. | | |
| Reactors A, B, C and D | 177 | 170 |
| Reactors B, F, G and H | 167 | 170 |

TABLE II

Analysis of Olefin-containing $C_3$–$C_4$ and Light Reformate Streams.

| Component or Property | Before Shutdown | After Shutdown |
| --- | --- | --- |
| Olefin-containing C3-C4 Stream Composition, vol. % | | |
| Methane | 0.0 | 0.0 |
| Ethane | 1.0 | 2.1 |
| Ethylene | 0.0 | 0.0 |
| Propane | 20.4 | 21.8 |
| Propene | 23.4 | 25.9 |
| Butane | 12.8 | 12.3 |
| 2-Methylpropane | 20.3 | 18.8 |
| $C_4$-Olefins | 20.4 | 19.1 |
| Pentane | 0.3 | 0.0 |
| 2-Methylbutane | 1.4 | 0.0 |
| Light Reformate Stream Composition, vol. % | | |
| Olefins | 1.5 | 1.5 |
| Aromatics | 33.5 | 34.2 |
| Saturated Hydrocarbons | 64.9 | 64.5 |
| Benzene | 7.1 | 7.2 |
| Distillation Properties, °F. (°C.) | | |
| T10 | 124 (51) | — |
| T50 | 177 (81) | — |
| T90 | 222 (106) | — |
| Final Boiling Point | 237 (114) | — |

TABLE III

Catalyst Activity Before and After Shutdown.

| Reactor | Catalyst Activity Before Shutdown | Catalyst Activity After Shutdown | Comments |
| --- | --- | --- | --- |
| A | 4.0 | 4.4 | — |
| B | 3.9 | 4.3 | — |
| C | — | — | Catalyst replaced during shutdown |
| E | 5.2 | 5.5 | — |
| F | 3.9 | 3.2–82% | — |
| G | — | — | Catalyst replaced during shutdown |
| H | 7.1 | 6.3–89% | Conventional procedure used for shutdown |

We claim:

1. A process for taking a fixed-bed of solid acid catalyst out of use without causing any significant catalyst deactivation, wherein said catalyst bed is used to catalyze the polymerization of olefins in an olefin-containing feedstock, and wherein said process comprises:
   (a) substituting a modified feedstock for the olefin-containing feedstock without terminating the flow of material through the catalyst bed, wherein said modified feedstock is prepared by substituting a substantially olefin-free hydrocarbon fluid for at least a portion of said olefin-containing feedstock, and wherein the substantially olefin-free hydrocarbon fluid boils within the range from about 20° to about 250° C. and contains at least about 5 vol. % aromatics; and
   (b) terminating the flow of said modified feedstock to the fixed-bed of catalyst after the contents of the fixed-bed have been displaced by the modified feedstock and any products derived from it, and wherein the amount of said substantially olefin-free hydrocarbon fluid used to prepare the modified feedstock is effective to prevent any significant deactivation of the fixed-bed of catalyst during said process.

2. The process of claim 1 which additionally comprises removing fluid hydrocarbons from the fixed-bed of catalyst after step (b).

3. The process of claim 1 wherein the modified feedstock contains from about 20 to about 70 vol. % of said substantially olefin-free hydrocarbon fluid.

4. The process of claim 1 wherein the mole ratio of olefins to aromatics in the modified feedstock is less than about 10.

5. The process of claim 1 wherein said catalyst is a solid phosphoric acid catalyst.

6. The process of claim 1 wherein a substantially constant material flow rate is maintained through the fixed-bed at olefin polymerization conditions while substituting said modified feedstock for said olefin-containing feedstock.

7. The process of claim 1 which additionally comprises reducing the temperature and pressure within said fixed-bed after step (b).

8. The process of claim 7 wherein the temperature within said fixed-bed is reduced to a value which is below that which is required to sustain rapid polymerization of the olefins in the olefin-containing feedstock.

9. The process of claim 7 wherein said fixed-bed of catalyst is subsequently put back into service for catalyzing the polymerization of olefins by the additional steps of:
   (a) adjusting the temperature and pressure of the fixed-bed of catalyst to a level suitable for olefin polymerization while said fixed-bed is filled with the modified feedstock;
   (b) displacing the modified feedstock with the olefin-containing feedstock at a flow rate suitable for olefin conversion; and
   (c) maintaining said flow of the olefin-containing feedstock under olefin polymerization conditions.

10. The process of claim 1 wherein the substantially olefin-free hydrocarbon fluid boils within the range from about 30° to about 130° C.

11. The process of claim 1 wherein said substantially olefin-free hydrocarbon fluid is selected from the group consisting of naphthas, reformates and blends of aromatic and aliphatic hydrocarbons.

12. The process of claim 1 wherein said substantially olefin-free hydrocarbon fluid contains at least about 20 vol. % aromatics.

13. The process of claim 1 wherein said substantially olefin-free hydrocarbon fluid contains from about 15 to about 85 vol. % aromatics.

14. The process of claim 1 wherein said substantially olefin-free hydrocarbon fluid is a reformate.

15. The process of claim 1 wherein said substantially olefin-free hydrocarbon fluid is substantially anhydrous.

16. The process of claim 1 wherein said olefin-containing feedstock is comprised of one or more olefins selected from the group consisting of olefins which contain from 3 to 6 carbon atoms.

17. The process of claim 16 wherein said olefin-containing feedstock is comprised of one or more olefins which are selected from the group consisting of olefins which contain from 3 to 4 carbon atoms.

18. The process of claim 16 wherein the product from said olefin polymerization is comprised of oligomers of said olefins.

19. The process of claim 1 wherein said olefin-containing feedstock is substantially free of aromatic hydrocarbons.

20. The process of claim 1 wherein said olefin-containing feedstock is additionally comprised of aromatic hydrocarbons and the mole ratio of olefins to aromatic hydrocarbons in said feedstock is at least about 15.

21. The process of claim 20 wherein said aromatic hydrocarbons contain from 6 to 10 carbon atoms.

22. The process of claim 1 wherein the product from said olefin conversion comprises products boiling in the gasoline range.

* * * * *

UNITED STATES PATENT AND TRADEMARK OFFICE
CERTIFICATE OF CORRECTION

PATENT NO. : 5,932,778

Page 1 of 2

DATED : Aug. 3, 1999

INVENTOR(S) : Anthony M. Valente, David B. Johnson, George A. Huff, Jr.

It is certified that error appears in the above-identified patent and that said Letters Patent is hereby corrected as shown below:

| Col. | Line | | |
|---|---|---|---|
| 3 | 11 | "from about 20°0 to" should read: "from about 20° to" | |
| 6 | 16 | "AICl$_3$" should read: "AlCl$_3$" | |
| 6 | 51 | "(Ipatieffet al.)" should read: "(Ipatieff et al.)" | |
| 12 | 38,39 | In the table, there should be a space between these two lines. | |
| 12 | 43,44 | In the table, there should be a space between these two lines. | |
| 11 | 58,59 | "(Reactors A, B, C, B, F, G and H)" should read: "7 (Reactors A, B, C, E, F, G and H)" | |

UNITED STATES PATENT AND TRADEMARK OFFICE
CERTIFICATE OF CORRECTION

PATENT NO. : 5,932,778
DATED : Aug. 3, 1999
INVENTOR(S) : Anthony M. Valente, David B. Johnson, George A. Huff, Jr.

It is certified that error appears in the above-identified patent and that said Letters Patent is hereby corrected as shown below:

| Col. | Line | |
|---|---|---|
| 12 | 20 | "Reactors B, F, G and H" <br><br> should read: <br> "Reactors E, F, G and H" |
| 12 | 62 | "F   3.9   3.2-82%   --" <br><br> should read: <br> "F   3.9   3.2   --" |
| 12 | 64 | "H   7.1   6.3-89%   Conventional procedure" <br><br> should read: <br> "H   7.1   6.3   Conventional procedure" |

Signed and Sealed this

Fifteenth Day of February, 2000

Attest:

Q. TODD DICKINSON

*Attesting Officer*     *Commissioner of Patents and Trademarks*